(12) United States Patent
Iwasaki et al.

(10) Patent No.: US 8,304,721 B2
(45) Date of Patent: Nov. 6, 2012

(54) MICRO CROSS-SECTION PROCESSING METHOD

(75) Inventors: Kouji Iwasaki, Chiba (JP); Tatsuya Adachi, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 486 days.

(21) Appl. No.: 12/708,896

(22) Filed: Feb. 19, 2010

(65) Prior Publication Data

US 2010/0215868 A1    Aug. 26, 2010

(30) Foreign Application Priority Data

Feb. 20, 2009  (JP) .................. 2009-037310

(51) Int. Cl.
*H01L 21/302* (2006.01)
*H01L 21/66* (2006.01)
*H01J 37/26* (2006.01)
*H01J 37/30* (2006.01)

(52) U.S. Cl. ........ 250/309; 250/304; 250/307; 250/310; 250/311

(58) Field of Classification Search .................. 250/304, 250/307, 309, 310, 311
See application file for complete search history.

(56) References Cited

U.S. PATENT DOCUMENTS 6,664,552 B2 * 12/2003 Shichi et al. .................. 250/307
7,005,640 B2 * 2/2006 Bloess .......................... 250/309
7,442,924 B2 * 10/2008 Giannuzzi et al. ............ 250/307

FOREIGN PATENT DOCUMENTS

JP             03-166744 A     7/1991

* cited by examiner

*Primary Examiner* — Jack Berman
(74) *Attorney, Agent, or Firm* — Brinks Hofer Gilson & Lione

(57) ABSTRACT

A micro cross-section processing method includes the steps of determining a linear cross-section estimated position including an observation object on a surface of the sample, irradiating the focused ion beam to the cross-section estimated position perpendicularly to or at a tilt angle to form a cross-section at a position in front of the cross-section estimated position, irradiating the focused ion beam to both ends of the cross-section to form side cuts extending to a position in rear of the cross-section estimated position, irradiating the focused ion beam to a position on the surface of the cross-section and at a position deeper than the observation object to form a bottom cut extending to a position in rear of the cross-section estimated position, irradiating the focused ion beam along from the side cuts to the cross-section estimated position to form wedges connecting to the bottom cut, and applying impact to a region in front of the cross-section estimated position of the sample to cleave the vicinity of the cross-section estimated position between the wedges and form a plane of cleavage.

4 Claims, 8 Drawing Sheets

MICRO CROSS-SECTION PROCESSING METHOD

RELATED APPLICATIONS

This application claims priority under 35 U.S.C. §119 to Japanese Patent Application No. 2009-037310 filed on Feb. 20, 2009, the entire content of which is hereby incorporated by reference.

BACKGROUND OF THE INVENTION

1. Field of the Invention

The present invention relates to a micro cross-section processing method, which may be used for observing a cross section of a semiconductor device, for example, and performs cross-section processing on a sample with a focused ion beam.

2. Description of the Related Art

Samples having minute patterns, such as a semiconductor device and a semiconductor laser device, are increasingly minute. Thus, those samples generally undergo cross-section processing with a focused ion beam (or FIB) for cross-section observation with an SEM. Recently, cross-section processing on a pattern of 100 nm or below has been required.

Accordingly, a technology (Japanese Patent No. 2973211) has been known that tilts a sample for cross-section observation, irradiates a focused ion beam thereto, exposes a cross-section of the sample, and then observes (or measures or analyzes) the cross-section by using a scanning ion microscope function of a focused ion beam system.

However, since the cross-section processing with FIB may damage the sample due to the beam, it is difficult to observe a material or structure susceptible to damage, which is a problem. Particularly, a p-n junction of a semiconductor may not appear clearly due to damage by FIB processing or finishing processing with argon ions, which is another problem.

On the other hand, hitherto, a method for preventing damage on a sample has been known that mechanically cleaving a sample to expose a cross-section thereof and acquire a clear cross-section SEM image thereby. However, it is significantly difficult to cleave a minute specific part.

SUMMARY OF THE INVENTION

The invention was made in order to solve the problems, and it is an object of the invention to provide a micro cross-section processing method that cleaves a minute specific part to acquire a cross-section thereof.

In order to achieve the object, there is provided, according to an aspect of the invention, a micro cross-section processing method that uses a focused ion beam system to irradiate a focused ion beam to a sample and performs cross-section processing on the sample, the method including a processing-estimated-position determining step of determining a linear cross-section estimated position including an observation object on a surface of the sample, a cross-section processing step of irradiating the focused ion beam to the cross-section estimated position with the direction of launching perpendicular to or at a tilt angle to the surface of the sample to form a cross-section at a position in front of the cross-section estimated position, a side-cut processing step of irradiating the focused ion beam to both ends of the cross-section to form side cuts extending to a position in rear of the cross-section estimated position at both ends, a bottom-cut processing step of irradiating the focused ion beam to a position on the surface of the cross-section and at a position deeper than the observation object to form a bottom cut extending to a position in rear of the cross-section estimated position and connecting to the side cuts, a wedge processing step of irradiating the focused ion beam along from the side cuts to the cross-section estimated position to form wedges extending inwardly from both ends of the cross-section and connecting to the bottom cut, and an observation-cross-section processing step of applying impact to a region in front of the cross-section estimated position of the sample to cleave the vicinity of the cross-section estimated position between the wedges and form a plane of cleavage.

With the configuration, the circumference (including the sides and the bottom) of the region to be cleaved of a sample is entirely removed by side cut and bottom cut, and the formed wedge can facilitate forming a plane of cleavage along the cross-section estimated position. Thus, a specific position (in the vicinity of the cross-section estimated position) even in a minute region can be cleaved.

The micro cross-section processing method may further include an overcoat forming step of, when the observation object is positioned on the sample surface, forming an overcoat to cover the observation object on the surface of the sample before irradiating the focused ion beam.

This configuration can suppress damage on the observation object due to the focused ion beam.

The wedge processing step may include separating the pointed ends of the wedges from the observation object by 0.5 μm or more.

This configuration can suppress damage on the observation object due to the focused ion beam.

The micro cross-section processing method may further include an observation-object position displaying step of, when the observation object is positioned inside the sample, displaying the position of the observation object on the surface of the sample before the processing-estimated-position determining step.

This configuration allows easy observation of the cross-section estimated position and facilitates involved operations when a focused ion beam system is used to perform micro-cross-section processing.

According to the invention, a minute specific part can be cleaved to acquire a cross-section thereof.

DETAILED DESCRIPTION OF THE PREFERRED EMBODIMENT

With reference to drawings, embodiments of the invention will be described below.

Figure 1:
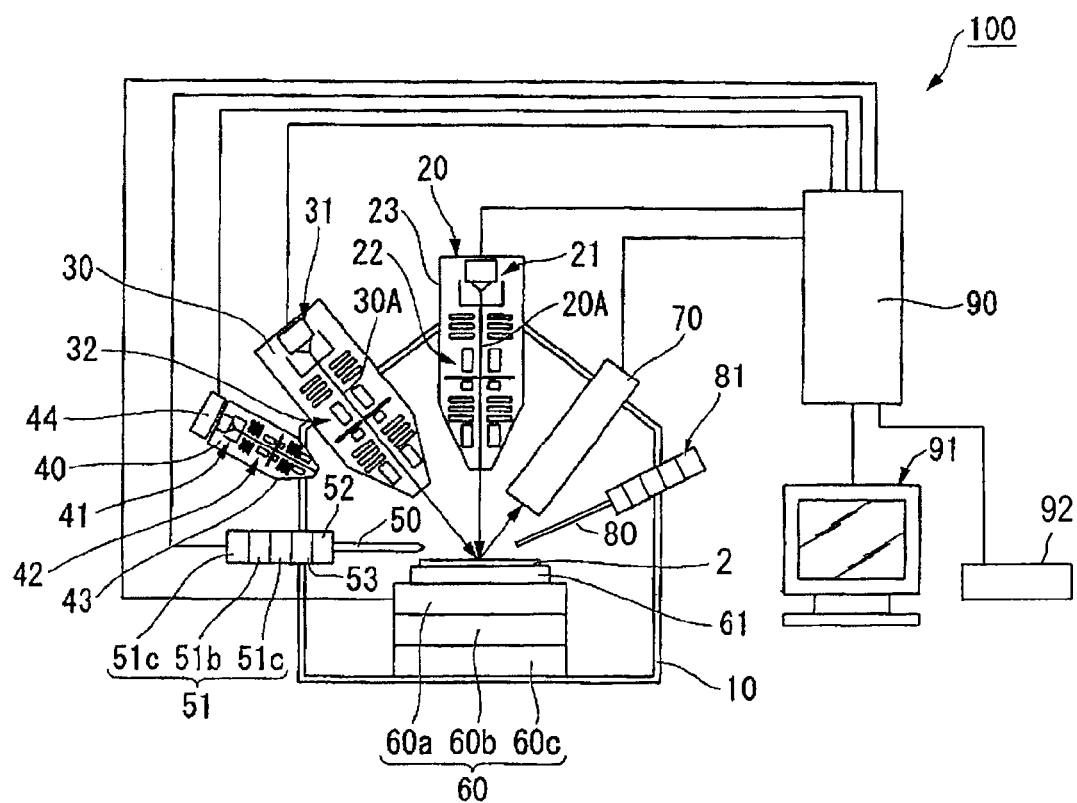
FIG. 1 is a block diagram illustrating an entire configuration of a focused ion beam system to be preferably used in the invention.

FIG. 1 is a block diagram illustrating the entire configuration of a focused ion beam system 100, which can be used for a micro cross-section processing method according to an embodiment of the invention. Referring to FIG. 1, the focused ion beam system 100 includes a vacuum chamber 10, an ion beam irradiating system 20, an electron beam irradiating system 30, an argon ion beam irradiating system 40, nanotweezers 50, a sample stage 60, a secondary charged particle detector 70, a microprobe 80, and a control portion 90. The interior of the vacuum chamber 10 is depressurized to a predetermined degree of vacuum, and a part or all of the components of the focused ion beam system 100 are placed within the vacuum chamber 10.

The sample stage 60 supports a sample base 61 movably, and a sample 2 is mounted on the sample base 61. The sample stage 60 has a moving mechanism that displaces the sample base 61 on five axes. The moving mechanism includes an XYZ moving mechanism 60b that moves the sample base 61 along an X-axis and a Y-axis, which are parallel with the horizontal plane and orthogonal to each other, and along a Z-axis, which is orthogonal to the X-axis and Y-axis, a rotating mechanism 60c that rotates the sample base 61 about the Z-axis, and a tilting mechanism 60a that rotates the sample base 61 about the X-axis (or Y-axis). The sample stage 60 may displace the sample base 61 on five axes so that the sample 2 can be moved to the irradiation position of an ion beam (or focused ion beam) 20A, and the ion beam 20A is irradiated at a predetermined angle to the sample 2.

The control portion 90 may be configured by a computer including a CPU (or central processing unit), a storing portion (such as a RAM and a ROM) 93 that stores data and/or programs, and an input port and output port for inputting and outputting a signal from and to an external apparatus. In the control portion 90, the CPU performs arithmetic processing on the basis of programs stored in the storing portion 93 so as to control the components of the focused ion beam system 100.

The control portion 90 further converts the secondary charged particles detected by the secondary charged particle detector 70 to a luminance signal, thus creates image data representing a sample surface and creates the sample image on the basis of the image data. The sample image is output to a display apparatus 91 connected to the control portion 90. An operator can perform micro cross-section processing on the display apparatus 91.

The control portion 90 further drives the sample stage 60 on the basis of a software instruction or operator's input and adjusts the position or attitude of the sample 2 so as to adjust the irradiation position and/or irradiation angle of the ion beam 20A to the surface of the sample 2. The control portion 90 further drives a microprobe stage 81 so as to adjust the position and/or attitude of the microprobe 80 including a microneedle, for example. Similarly, the control portion 90 drives a tweezers stage 51 and a holding mechanism 53 so as to adjust the position and/or attitude of the nanotweezers 50 and grasp the sample 2 with the nanotweezers 50.

The control portion 90 is connected to input means 92 such as a keyboard for acquiring an instruction input by an operator.

The ion beam irradiating system 20 includes an ion source 21 that generates ions and an ion optical system 22 that forms the ions outflowing from the ion source 21 into a focused ion beam and scans the focused ion beam. The ion beam 20A being a charged particle beam is irradiated from the ion beam irradiating system 20 including an ion beam tube 23 to the sample 2 on the sample stage 60 within the vacuum chamber 10. Here, from the sample 2, secondary charged particles such as secondary ions and secondary electrons are generated. The secondary charged particles are detected by the secondary charged particle detector 70, and an image of the sample 2 is acquired. The ion beam irradiating system 20 may increase the intensity of the ion beam 20A so as to perform etching processing on the sample 2 in the irradiation range.

The ion optical system 22 may include, for example, a condenser lens that focuses the ion beam 20A, an aperture that narrows the ion beam 20A, an aligner that adjusts the optical axis of the ion beam 20A, an objective lens that focuses the ion beam 20A to a sample, and a deflector that scans the ion beam 20A on the sample.

The electron beam irradiating system 30 includes an electron source 31 that emits electrons and an electron-optical system 32 that forms the electrons emitted from the electron source 31 into a beam and scans the beam. Due to the irradiation of the electron beam 30A emitted from the electron beam irradiating system 30 to the sample 2, the sample 2 generates secondary electrons. The generated secondary electrons may be detected by the secondary charged particle detector 70 to acquire an image of the sample 2. Here, the electron beam 30A emitted from the electron beam tube 33 is irradiated onto the sample 2 at the same irradiation position as that of the ion beam 20A.

In order to acquire a sample image rendering a sample surface, the secondary charged particles (such as secondary ions and secondary electrons) generated by the irradiation of the ion beam 20A may be used, or the secondary charged particles (such as secondary electrons) generated by the irradiation of the electron beam 30A may be used. However, according to the invention, in order to suppress damage on the sample due to the irradiation of the ion beam 20A, secondary electrons by the electron beam irradiating system 30 are preferably used for observation of the sample.

The argon ion beam irradiating system 40 includes an argon ion source 41, an argon ion optical system 42, and an argon ion beam tube 43 and further includes beam-position control means 44 for controlling the irradiation position of an argon ion beam. The argon ion beam irradiating system 40 irradiates an argon ion beam for cleaning the sample 2.

When the ion beam 20A or electron beam 30A is irradiated to the original sample 2, the secondary charged particle detector 70 detects the secondary charged particles (such as secondary electrons and secondary ions) reflected from the sample 2.

Next, a micro cross-section processing method according to an embodiment of the invention will be described.

Figure 2:
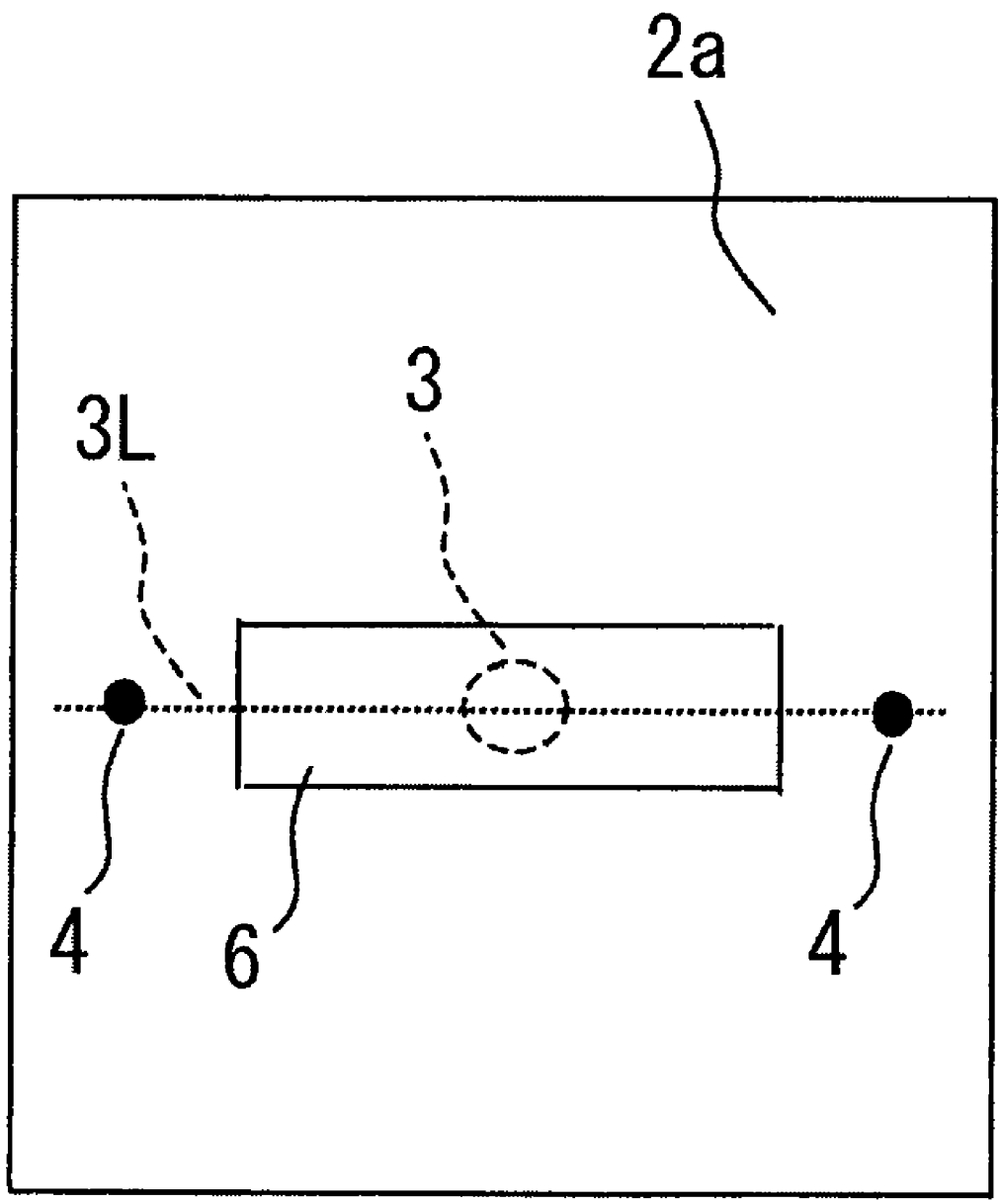
FIG. 2 is a top view illustrating a processing-estimated-position determining step.

FIG. 2 illustrates a processing-estimated-position determining step of determining a linear cross-section estimated position 3L including an observation object 3 on a sample surface 2a. The cross-section estimated position 3L indicates a position of the cross-section to be a plane of cleavage, which will be described later. An operator designates the cross-section estimated position 3L on the display device 91. The control portion 90 acquires and stores the coordinates of the cross-section estimated position 3L on the display device 91 and displays the cross-section estimated position 3L on the display device 91 during processing.

The sample 2 may be a semiconductor device, for example. The observation object 3 may be a failing part within the semiconductor device, for example.

The size of the object region (plane of cleavage) of the sample 2 to be processed by the invention is not particularly limited, but a region approximately several μm or smaller (such as 1.5 to 2 μm or smaller) wide and deep may be cleaved.

When the observation object 3 is positioned on the sample surface 2a, an overcoat 6 to cover the observation object 3 may be formed on the sample surface 2a (overcoat forming step) before the ion beam 20A is irradiated thereto. The overcoat 6 may be a carbon or tungsten overcoat, which can be formed by a local positioning function with the irradiation of the focused ion beam 20A or the irradiation of the electron beam 30A in the focused ion beam system 100 and gas supply from a gas supply system (not shown).

On the other hand, when the observation object 3 is positioned within the sample 2, the position of the observation object 3 may be displayed on the sample surface 2a (observation-object position displaying step) before the processing-estimated-position determining step. The position of the observation object 3 may be stored in the control portion 90 with the cross-section estimated position 3L being a segment connecting laser markers 4 impressed at two positions on the sample surface 2a or an operator can recognize the segment connecting the laser markers 4 on the display apparatus 91. Alternatively, a CAD linkage may be used to display the position of the observation object 3 on the sample surface 2a.

The observation-object position displaying step allows an operator to adjust so as to prevent the etching processing with the ion beam 20a beyond the cross-section estimated position 3L by watching the display apparatus 91 in the steps that will be described later.

Figure 3:
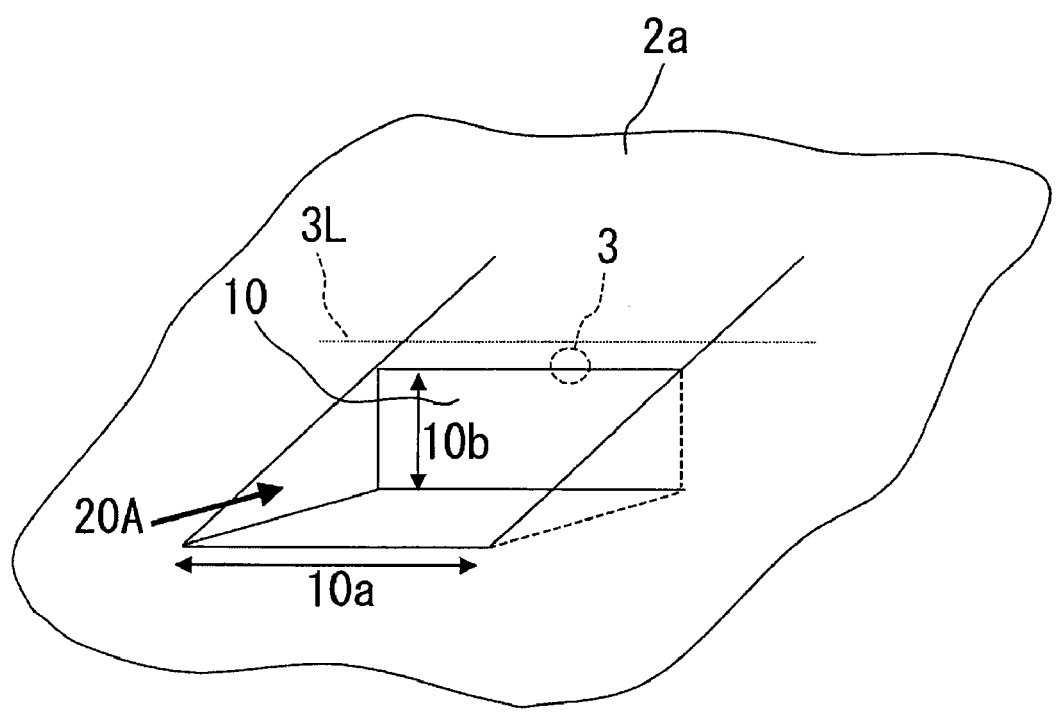
FIG. 3 is a diagram illustrating a cross-section processing step.

Next, as illustrated in FIG. 3, the ion beam 20A is irradiated to the cross-section estimated position 3L with the direction of the launched beam perpendicularly or at a tilt angle to the sample surface 2a, and a cross-section 10 is formed at a position in front of the cross-section estimated position 3L (or on the launching side of the ion beam 20A) (cross-section processing step).

The cross-section 10 may be at a right angle to the sample surface 2a. A slanting surface is formed from the sample surface 2a through the inside of the sample at the tilt angle to the cross-section 10. The depth 10b of the cross-section 10 is deeper than the depth from the sample surface 2a to the observation object 3, and the cross-section 10 has a width 10a.

The cross-section 10 is formed by performing cross-section processing on a part in front of the cross-section estimated position 3L (such as the part 0.5 µm to several µm before the cross-section estimated position 3L) such that the cross-section estimated position 3 can be the plane of cleavage. The cross-section processing may be performed such that the width 10a of the cross-section 10 can be larger by several µm in the left and right directions than the width of the plane of cleavage. The depth 10b of the cross-section 10 may be deeper by several µm than the depth of the plane of cleavage.

Figure 4:
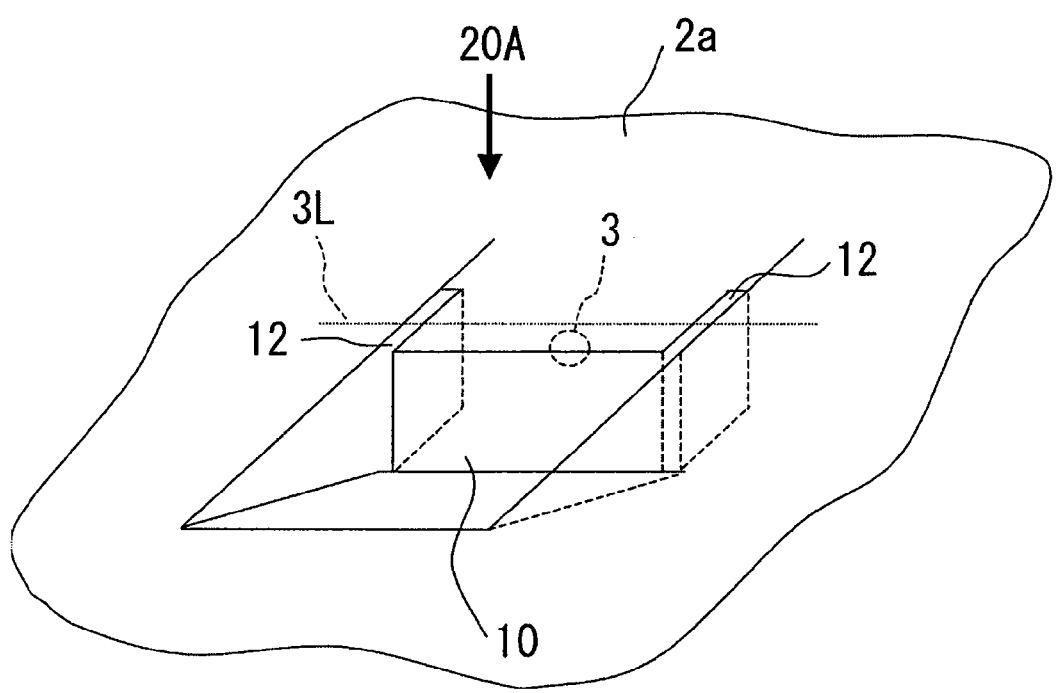
FIG. 4 is a diagram illustrating a side-cut processing step.

Next, as illustrated in FIG. 4, the ion beam 20A is irradiated to both ends of the cross-section 10, and side cuts 12 and 12 extending to a rear position of the cross-section estimated position 3L are formed on both ends of the cross-section 10 in the direction of the width 10a (side-cut processing step).

The side cuts 12 and 12 may only be required to extend to a rear position of the cross-section estimated position 3L by 0.5 to several µm (or on the rear side of the cross-section 10). The depths of the side cuts 12 and 12 may only be required to be deeper than the observation object 3 by the order of several µm, for example. The side cuts 12 and 12 may connect to the bottom of the cross-section 10 or may be shallower than the bottom of the cross-section 10. The widths of the side cuts 12 and 12 may be 0.5 µm to several µm, for example.

The side cuts 12 and 12 facilitate cleaving by separating a region 2x, which will be described later, to be cleaved from the body of the sample 2.

Figure 5:
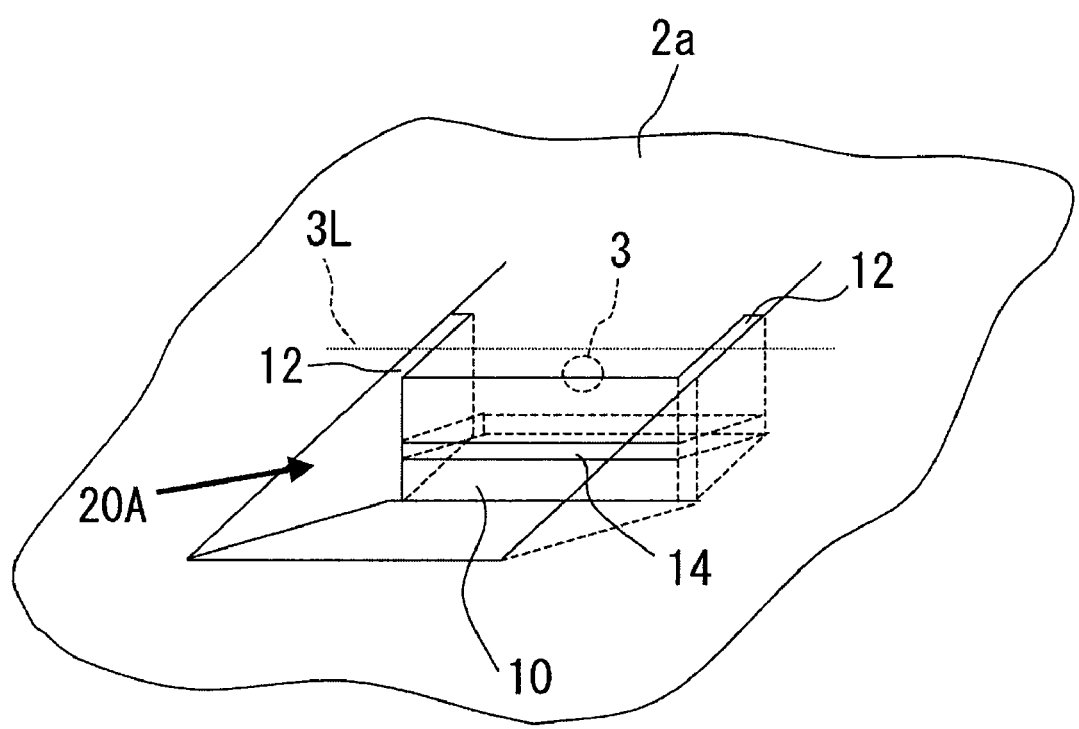
FIG. 5 is a diagram illustrating a bottom-cut processing step.

Next, as illustrated in FIG. 5, the ion beam 20A is irradiated to the position that is on the surface of the cross-section 10 and is deeper than the observation object 3 to form a bottom cut 14 that extends to a position in rear of the cross-section estimated position 3L and connects to the side cuts 12 and 12 (bottom-cut processing step).

This can facilitate cleaving by separating the region 2x to be cleaved from the bottom of the sample 2 and holding the region 2x only at the rear face of the sample 2.

The irradiation angle of the ion beam 20A in the bottom-cut processing step is not particularly limited, but the processing will be easier if it is substantially equal to the irradiation angle in the cross-section processing step.

Figure 6:
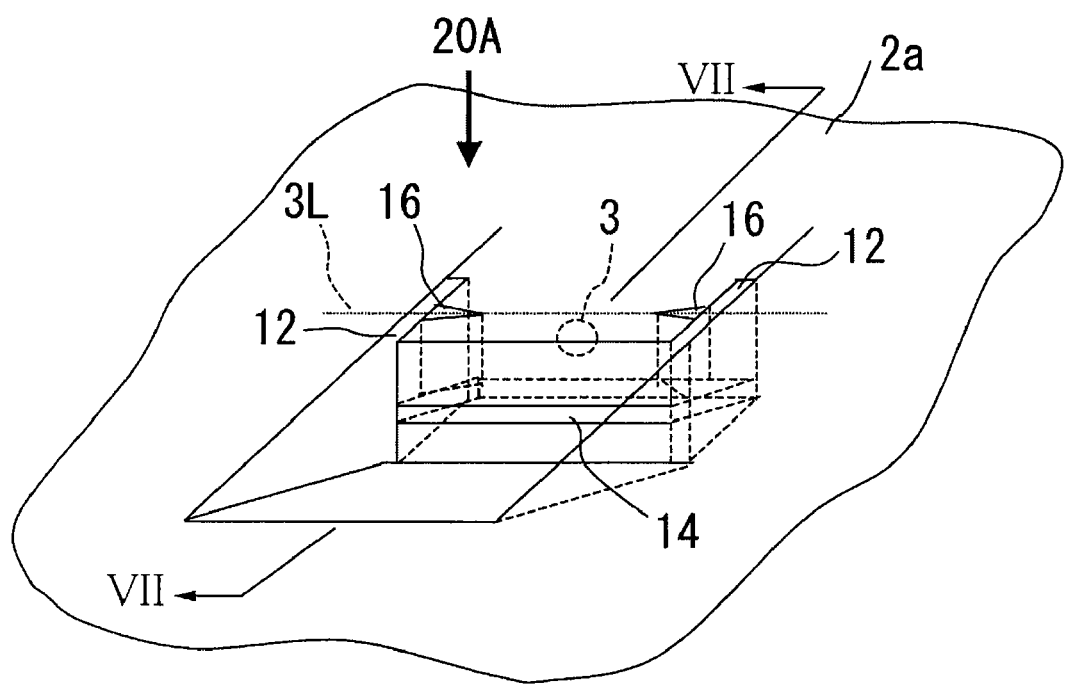
FIG. 6 is a diagram illustrating a wedge processing step.

Next, as illustrated in FIG. 6, the ion beam 20A is irradiated along from the side cuts 12 and 12 to the cross-section estimated position 3L to form wedges 16 and 16 that extend inwardly from both ends of the cross-section 10 to the cross-section estimated position 3L and connect along the bottom cut 14 (wedge processing step). Each of the wedges 16 and 16 is formed to have a pointed end inwardly from both ends of the cross-section 10.

However, a distance between the pointed end of the wedge 16 and the observation object 3 is preferably equal to the order of 0.5 to 1 µm so as to prevent the ion beam 20A from damaging the observation object 3 in forming the wedge 16.

In this way, when the entire surrounding part (including the sides and bottom) of the region 2x to be cleaved is removed and the wedges 16 and 16 are formed, the plane of cleavage can easily appear along the cross-section estimated position 3L thereby. Thus, even a specific position (in the vicinity of cross-section estimated position 3L) in a minute region can be cleaved.

Figure 7:
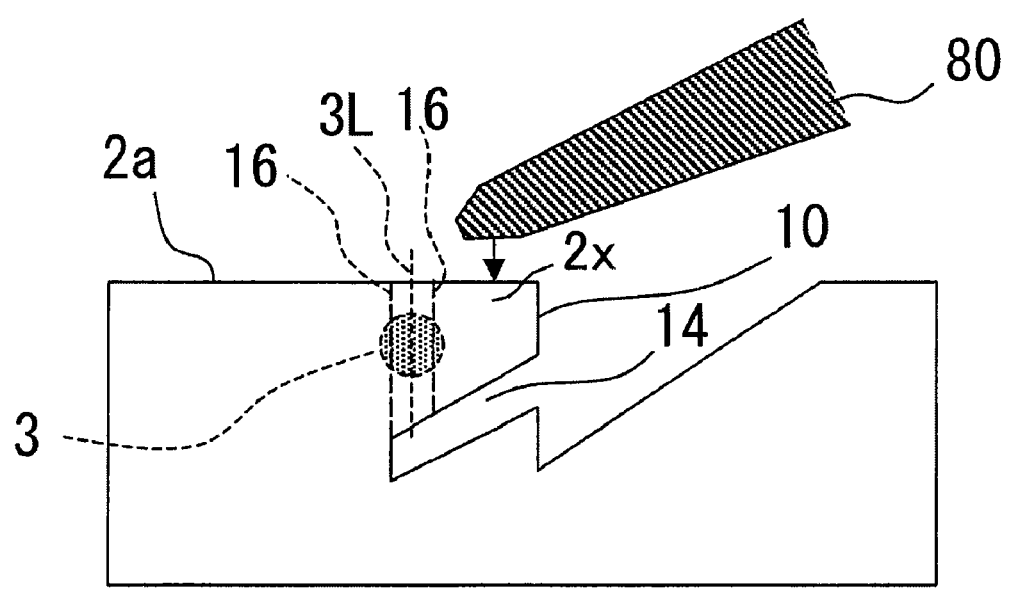
FIG. 7 is a section view taken in the line VII-VII in FIG. 6.

FIG. 7 illustrates a section view, which is taken on the line VII-VII in FIG. 6, of the sample 2 after the wedge processing step ends. As illustrated in FIG. 7, when the surface of the region 2x in front of the cross-section estimated position 3L of the sample 2 is hit with a microprobe 80 to apply impact thereto, the region 2x floating between the wedges 16 and 16 with the entire surrounding part (including the sides and bottom) removed is cleaved and falls off.

Figure 8:
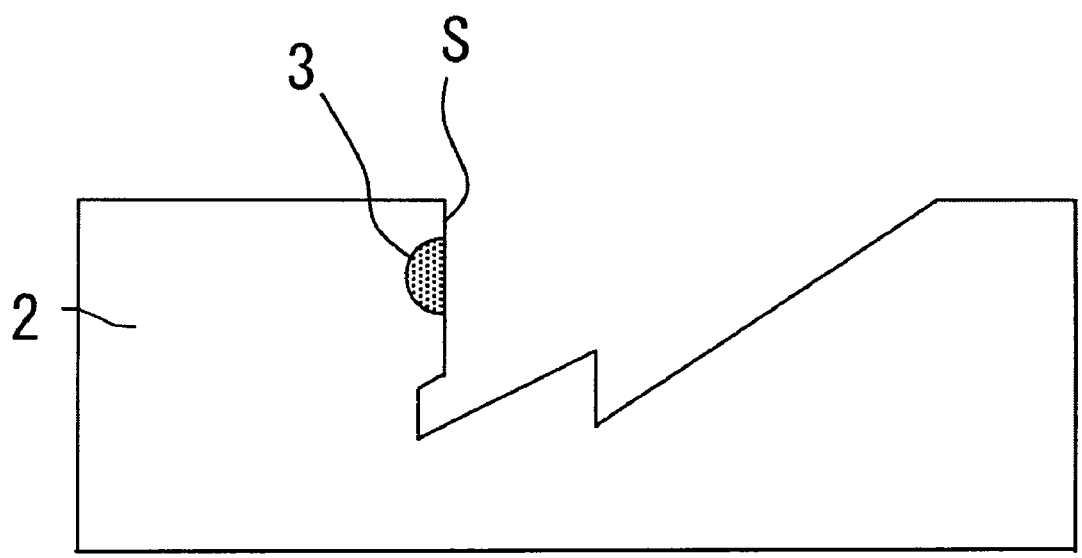
FIG. 8 is a diagram illustrating an observation-cross-section processing step.

Thus, as illustrated in FIG. 8, the plane of cleavage S is exposed in the vicinity of the cross-section estimated position 3L (observation-cross-section processing step).

The method for applying impact to the region 2x may include grasping the region 2x with the nanotweezers 50 and moving the nanotweezers 50 in the horizontal and vertical directions.

In this way, a minute specific part (of several µm or smaller vertically and horizontally, for example) may be cleaved to acquire a cross-section thereof. In order to prevent the irradiation of the ion beam 20A to the cross-section after the cleaving, the observation on the sample 2 in the observation-cross-section processing step may preferably be performed with the electron beam irradiating system 30.

The invention is not limited to the embodiments but includes various changes and equivalents without departing from the spirit and scope of the invention.

For example, when the observation object 3 exists in a deep part of the sample 2 and the region to be cleaved positions in a deeper part than the sample surface 2a, the sample surface 2a may be shaved in advance with the ion beam 20A.

What is claimed is:

1. A micro cross-section processing method that uses a focused ion beam system to irradiate a focused ion beam to a sample and performs cross-section processing on the sample, the method comprising:
   a processing-estimated-position determining step of determining a linear cross-section estimated position including an observation object on a surface of the sample;
   a cross-section processing step of irradiating the focused ion beam to the cross-section estimated position with the direction of launching perpendicular to or at a tilt angle to the surface of the sample to form a cross-section at a position in front of the cross-section estimated position;
   a side-cut processing step of irradiating the focused ion beam to both ends of the cross-section to form side cuts extending to a position in rear of the cross-section estimated position at both ends;
   a bottom-cut processing step of irradiating the focused ion beam to a position on the surface of the cross-section and at a position deeper than the observation object to form a bottom cut extending to a position in rear of the cross-section estimated position and connecting to the side cuts;
   a wedge processing step of irradiating the focused ion beam along from the side cuts to the cross-section estimated position to form wedges extending inwardly from both ends of the cross-section and connecting to the bottom cut; and
   an observation-cross-section processing step of applying impact to a region in front of the cross-section estimated position of the sample to cleave the vicinity of the cross-section estimated position between the wedges and form a plane of cleavage.

2. The micro cross-section processing method according to claim 1, the method further comprising an overcoat forming step of, when the observation object is positioned on the sample surface, forming an overcoat to cover the observation object on the surface of the sample before irradiating the focused ion beam.

3. The micro cross-section processing method according to claim 1, wherein the wedge processing step includes separating the pointed ends of the wedges from the observation object by 0.5 μm or more.

4. The micro cross-section processing method according to claim 1, further comprising an observation-object position displaying step of, when the observation object is positioned inside the sample, displaying the position of the observation object on the surface of the sample before the processing-estimated-position determining step.

* * * * *